(12) United States Patent
Cantrell, Jr.

(10) Patent No.: US 9,873,689 B2
(45) Date of Patent: Jan. 23, 2018

(54) SYNTHESIS OF FATOSTATIN BASED POLYCYCLIC COMPOUNDS

(71) Applicant: FGH BIOTECH, INC., Houston, TX (US)

(72) Inventor: William R. Cantrell, Jr., San Antonio, TX (US)

(73) Assignee: FGH BIOTECH, INC., Houston, TX (US)

( * ) Notice: Subject to any disclaimer, the term of this patent is extended or adjusted under 35 U.S.C. 154(b) by 0 days.

(21) Appl. No.: 14/934,279

(22) Filed: Nov. 6, 2015

(65) Prior Publication Data

US 2016/0130264 A1   May 12, 2016

Related U.S. Application Data

(60) Provisional application No. 62/076,844, filed on Nov. 7, 2014.

(51) Int. Cl.
*C07D 417/04* (2006.01)
*C07D 417/14* (2006.01)

(52) U.S. Cl.
CPC .................. *C07D 417/04* (2013.01)

(58) Field of Classification Search
CPC ..................... C07D 417/04; C07D 417/14
USPC .............................................. 546/153, 270.4
See application file for complete search history.

(56) References Cited

FOREIGN PATENT DOCUMENTS

| WO | WO 2008/097835 | 8/2008 |
|---|---|---|
| WO | WO 2015/031650 | 3/2015 |

OTHER PUBLICATIONS

Bellale, et al., "Diarylthiazoles, etc.," Supplementary information, J. Med. Chem., 201457, 6572-6582.*
Bellale, Eknath et al., "Diarylthiazole: An Antimycobacterial Scaffold Potentially Targeting PrrB-PrrA Two-Component System," J. Med. Chem., 2014, 57, pp. 6572-6582.
DataBase Registry [online] RN 298197-07-6, Oct. 23, 2000. Retrieved from STN.
International Search Report and Written Opinion of PCT/US2015/059411 dated Mar. 3, 2016; 6 pages.

* cited by examiner

*Primary Examiner* — Patricia L Morris
(74) *Attorney, Agent, or Firm* — Squire Patton Boggs (US) LLP

(57) ABSTRACT

The present invention relates to methods and strategies for large-scale synthesis of compounds having the chemical structure:

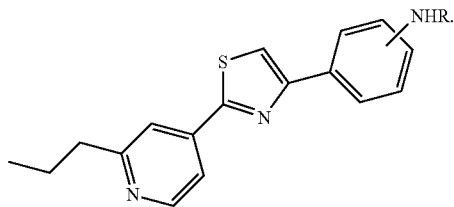

The R substituents are H, methyl, isopropyl, benzyl, cyclohexyl, cyclopropylmethyl, methoxy, tert-butyloxycarbonyl, methanesulfonyl, p-toluenesulfonyl, quinolinesulfonyl, or thiophenesulfonyl groups. The method comprises condensing prothionamide with a halo nitroacetophenone to form a nitrophenyl substituted thiazole, reducing the nitro group to form an amine and derivatizing the amine to produce the compound.

15 Claims, 1 Drawing Sheet

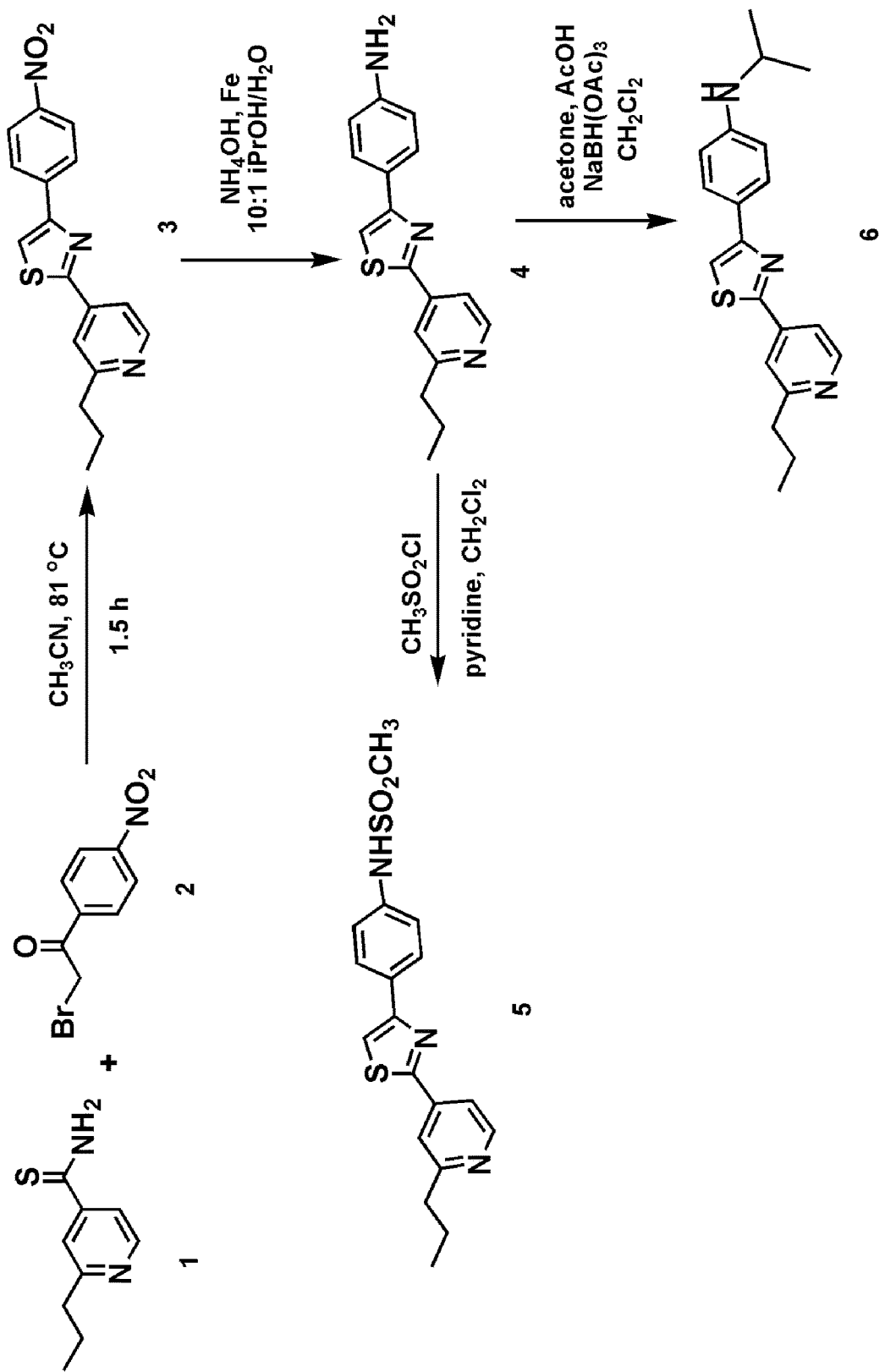

SYNTHESIS OF FATOSTATIN BASED POLYCYCLIC COMPOUNDS

CROSS-REFERENCE TO RELATED APPLICATIONS

This non-provisional application claims benefit of priority under 35 U.S.C. § 119(e) of provisional application U.S. Ser. No. 62/076,844, filed Nov. 7, 2014, the entirety of which is hereby incorporated by reference.

BACKGROUND OF THE INVENTION

Field of the Invention

The present invention generally relates to the chemical synthesis of substituted thiazole derivatives. Specifically, the present invention relates to the chemical synthesis of fatostatin A and its analogs or derivatives.

Description of the Related Art

Metabolic syndrome covers many cardiovascular risk factors including hypertension, dyslipidaemia, obesity, type 2 diabetes, pancreatic β-cell dysfunction, and atherosclerosis. A diet varying in fat or carbohydrate contents contributes to energy metabolism of animals including humans. Long chain fatty acids are major source of energy and important components of the lipids that comprise the cellular membranes. They are derived from food and synthesized de novo from acetyl-CoA. Cholesterol is also derived from food and synthesized from acetyl-CoA. The conversion of carbohydrates into acylglycerides through de novo fatty acid and cholesterol synthesis involves at least 12 and 23 enzymatic reactions, respectively. Expression levels of the genes encoding these enzymes are controlled by three transcription factors, designated sterol regulatory element-binding proteins (SREBPs), SREBP-1a, -1c and SREBP-2. These membrane-bound proteins are members of a class of the basic helix-loop-helix leucin zipper family of transcription factors. Unlike other leucin zipper members of transcription factors, sterol regulatory element-binding proteins are synthesized as an ER-membrane-bound precursor, which needs to be proteolytically released by two proteases bound to the Golgi membrane, Site-1 and Site-2 proteases, in order to activate transcription of target genes in the nucleus.

The proteolytic activation of sterol regulatory element-binding proteins is tightly regulated by sterols through the interaction with sterol regulatory element-binding protein cleavage-activating protein (SCAP), an ER-membrane-bound escort protein of sterol regulatory element-binding proteins. When sterols accumulate in the ER membranes, the SCAP/SREBP complex fails to exit the ER to the Golgi, and thereby the proteolytic processing of sterol regulatory element-binding proteins is suppressed. Sterol regulatory element-binding proteins are key lipogenic transcription factors that govern the homeostasis of fat metabolism.

Fatostatin is identified as an inhibitor of sterol regulatory element-binding protein activation. Fatostatin impairs the proteolytic activation of sterol regulatory element-binding proteins, thereby decreasing the transcription of lipogenic genes in cells. There is a recognized need in the for the development of efficient methods and strategies for producing substantially pure fatostatin derivatives or analogs in large quantities for gaining further insights into the regulation of sterol regulatory element-binding protein in order to develop drugs. The present invention fulfills this need.

SUMMARY OF THE INVENTION

The present invention is directed to a method for synthesizing a polycyclic derivative of a thiazole. The method comprises the steps of synthesizing a nitrophenyl substituted thiazole having the chemical structure

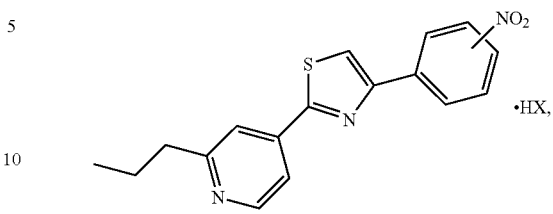

where X is a halogen, and then reducing the nitro group to form an amine. The amine is derivatized to produce the polycyclic thiazole derivative. The present invention is directed to a related method further comprising the step of recovering the polycyclic thiazole derivative.

The present invention also is directed to a method for synthesizing a fatostatin analog compound having the chemical structure:

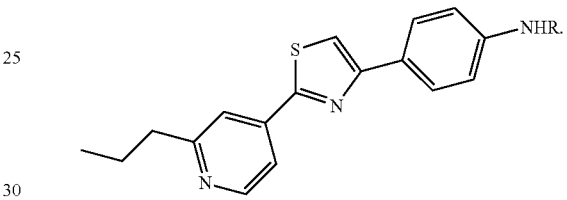

The R substituents may be H, methyl, isopropyl, benzyl, cyclohexyl, cyclopropylmethyl, -acetyl, tert-butyloxycarbonyl, methanesulfonyl, p-toluenesulfonyl, quinolinesulfonyl, or thiophenesulfonyl. The method comprises condensing prothionamide with a halo nitroacetophenone to form a nitrophenyl substituted thiazole having the chemical structure

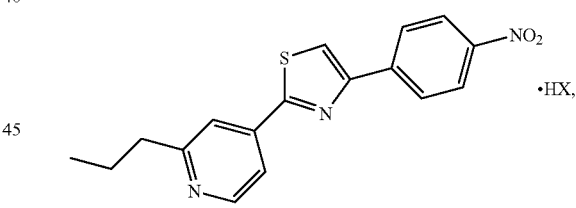

where X is a halogen and reducing the nitro group to form an amine. The amine is derivatized to produce the fatostatin analog compound. The present invention is directed to a related method further comprising the step of recovering the fatostatin analog compound.

The present invention is directed further to a compound having the chemical structure

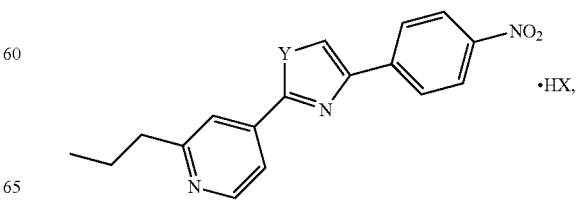

The X group may be bromine or chlorine and the Y substituent may be S or O.

Other and further aspects, features, benefits, and advantages of the present invention will be apparent from the following description of the presently preferred embodiments of the invention given for the purpose of disclosure.

BRIEF DESCRIPTION OF THE DRAWINGS

So that the matter in which the above-recited features, advantages and objects of the invention, as well as others that will become clear, are attained and can be understood in detail, more particular descriptions of the invention briefly summarized above may be had by reference to certain embodiments thereof that are illustrated in the appended drawings. These drawings form a part of the specification. It is to be noted, however, that the appended drawings illustrate preferred embodiments of the invention and therefore are not to be considered limiting in their scope.

FIG. 1 is a scheme for a large-scale synthesis of N-(4-(2-(2-propylpyridin-4-yl)thiazol-4-yl)phenyl)methanesulfonamide (5) and N-isopropyl-4-(2-(2-propylpyridin-4-yl)thiazol-4-yl)benzenamine (6).

DETAILED DESCRIPTION OF THE INVENTION

As used herein in the specification, "a" or "an" may mean one or more. As used herein in the claim(s), when used in conjunction with the word "comprising", the words "a" or "an" may mean one or more than one.

As used herein "another" or "other" may mean at least a second or more of the same or different claim element or components thereof. Similarly, the word "or" is intended to include "and" unless the context clearly indicates otherwise. "Comprise" means "include."

As used herein, the term "about" refers to a numeric value, including, for example, whole numbers, fractions, and percentages, whether or not explicitly indicated. The term "about" generally refers to a range of numerical values (e.g., +/−5-10% of the recited value) that one of ordinary skill in the art would consider equivalent to the recited value (e.g., having the same function or result). In some instances, the term "about" may include numerical values that are rounded to the nearest significant figure.

In one embodiment of the present invention, there is provided a method for synthesizing a polycyclic derivative of a thiazole, comprising the steps of: (a) synthesizing a nitrophenyl substituted thiazole having the chemical structure

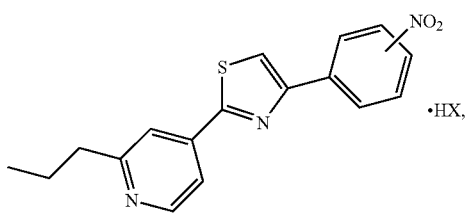

wherein X is a halogen; (b) reducing the nitro group to form an amine; and (c) derivatizing the amine to produce the polycyclic thiazole derivative. Further to this embodiment, the method may comprise recovering the polycyclic thiazole derivative.

In one aspect of both embodiments, the synthesizing step (a) may comprise condensing prothionamide with a halo nitroacetophenone to form the nitrophenyl substituted thiazole. In this aspect the condensing step may comprises heating a mixture of about 1:1 mole ratio of the prothionamide and the halo nitroacetophenone in acetonitrile. In a non-limiting example, the halo nitroacetophenone is 2-bromo-4'-nitroacetophenone.

In another aspect of both embodiments, any suitable reduction conditions for the reduction of the nitro groups can be used. For example, a representative reducing step comprises reacting the nitro group with an iron metal and catalytic ammonium hydroxide.

In these aspects and embodiments, a preferred polycyclic thiazole derivative may have the chemical structure:

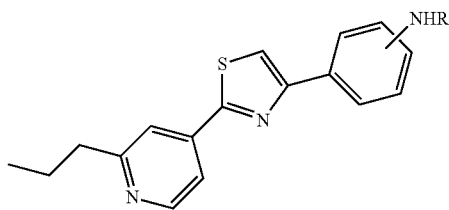

where R is H, isopropyl, benzyl, cyclohexyl, cyclopropylmethyl, acetyl (—C(O)CH$_3$), tert-butyloxycarbonyl, methanesulfonyl, p-toluenesulfonyl, quinolinesulfonyl, or thiophenesulfonyl. Preferable polycyclic thiazole derivatives have the chemical structures

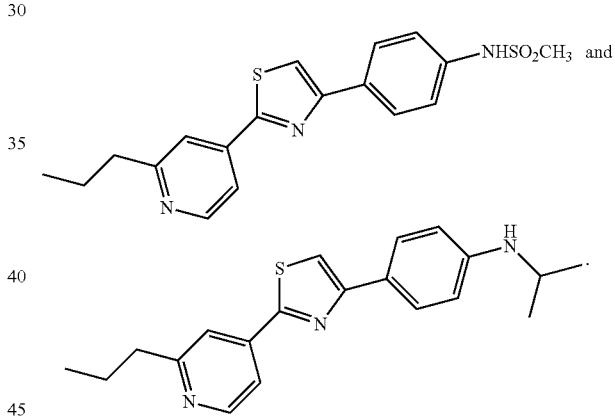

In another embodiment of this invention, there is provided a method for synthesizing a fatostatin analog compound having the chemical structure:

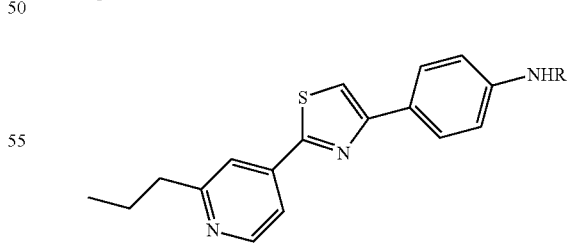

where R is H, methyl, isopropyl, benzyl, cyclohexyl, cyclopropylmethyl, acetyl (—C(O)CH$_3$), tert-butyloxycarbonyl, methanesulfonyl, p-toluenesulfonyl, quinolinesulfonyl, or thiophenesulfonyl and the method comprises the steps of: (a) condensing prothionamide with a halo nitroacetophenone to form a nitrophenyl substituted thiazole having the chemical structure

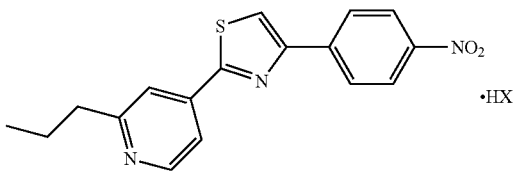
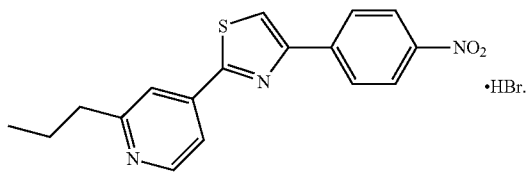

wherein X is a halogen; (b) reducing the nitro group to form an amine; and (c) derivatizing said amine to produce the fatostatin analog compound. Further to this embodiment the method comprises recovering the fatostatin analog compound.

In one aspect of both embodiments, the halo nitroacetophenone may be 2-bromo-4'-nitroacetophenone and the condensing step (a) comprises heating a mixture of the prothionamide and the 2-bromo-4'-nitroacetophenone in acetonitrile in a mole ratio of about 1:1.

In another aspect of both embodiments, the derivatizing step (c) may comprise reacting the amine with methanesulfonyl chloride and a base to produce the fatostatin analog compound. Any suitable base can be contemplated. In this aspect, the base may be pyridine. Also in this aspect, a representative fatostatin analog compound has the chemical structure

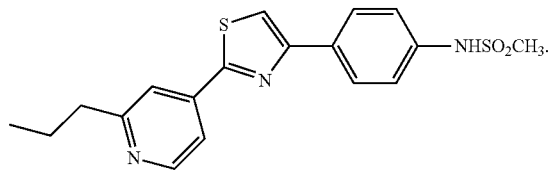

In yet another aspect, the derivatizing step (c) may comprise reductively aminating carbonyl compounds with the amine in the presence of a reducing agent to produce the compound. In this aspect, the carbonyl compound may be acetone and the reducing agent may be sodium triacetoxyborohydride. Also in this aspect, the fatostatin analog compound may be

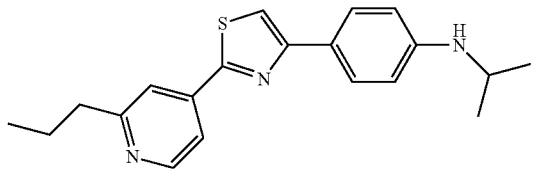

In yet another embodiment of this invention, there is provided a compound having the chemical structure:

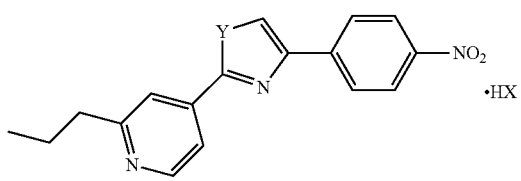

where X is bromine or chlorine; and Y is S or O. In a preferred example, the compound has the chemical structure Provided herein are methods and strategies for the large-scale synthesis of fatostatin analog and derivative compounds. Synthesis of fatostatin analogs or derivatives is accomplished using the synthetic scheme or strategy as shown in FIG. 1. Generally, the synthesis commences with the reaction of prothionamide 1 with 2-bromo-4'-nitroacetophenone (2) to form the thiazole derivative 3. The nitro group is converted to an amine by using reduction conditions ($NH_4OH/Fe$) to yield the amine 4. The amine is protected as methanesulfonamide 5 by reaction with methanesulfonyl chloride in the presence of a base, for example, but not limited to, pyridine). Alternatively, the amine 4 is subjected to reductive amination conditions with acetone in the presence of sodium triacetoxyborohydride to provide the isopropyl amine 6. Thus, also provided are the polycyclic thiazoles and the fatostatin analog compounds synthesized by this method.

The following examples are given for the purpose of illustrating various embodiments of the invention and are not meant to limit the present invention in any fashion.

EXAMPLE 1

Synthesis of 4-(4-(4-Nitrophenyl)-1,3-thiazol-2-yl]-2-propylpyridine hydrobromide 3

An 18 liter round bottom reactor, equipped with mechanical stirring, electrical heating, reflux condenser, and nitrogen purge, was charged with 2-propylpyridine-4-carbothioamide (1, 211.04 g, 1171 mmol), 2-bromo-1-(4-nitrophenyl)ethanone (2, 299.98 g, 1229 mmol) in acetonitrile (2.825 kg). The mixture was stirred under nitrogen and was heated to 81° C. After 1.5 h, additional acetonitrile (1.0 kg) was transferred to the reaction to aid stirring. After 4 hours, analysis (tlc) showed completion of the reaction. The reaction was cooled using an ice bath to less than 30° C. The solids were filtered and washed with acetonitrile (500 g). The product was transferred to a glass pan and was dried under vacuum at 50° C. with nitrogen purge flow for 18 hours. The solids were then manually broken up and the product was allowed to dry an additional 4 hours prior to weighing to plastic jars. The product was obtained as a fluffy yellow solid (461.7 g, 97%). $^1$H NMR (400 MHz, DMSO), δ 8.84 (m, 2H), 8.47 (s, 1H), 8.32 (m, 5H), 3.01 (t, 2H, J=7 Hz), 1.79 (m, 2H), 0.95 (t, 3H, J=7 Hz). MS $[M+H]^+$=326 m/z.

EXAMPLE 2

Synthesis of 4-[2-(2-Propylpyridin-4-yl)-1,3-thiazol-4-yl]aniline 4

An 18 liter round bottom reactor, equipped with mechanical stirring, electrical heating, reflux condenser, and nitrogen purge, was charged with compound 3 (449.14 g, 1105 mmol), ammonium hydroxide (32.87 g, 276 mmol), and 10% water in isopropanol (4.0 kg). A color change from yellow to pink was evidenced upon the addition of ammonium hydroxide reagent. The mixture was stirred under nitrogen and was heated to 60° C. A slight exotherm was observed. The reaction was allowed to stir for 1 h, when TLC (acetone/hexanes 1:1) showed that the reaction was complete. The reaction was allowed to cool for 2.5 h to room temperature, filtered and the insoluble solids were washed with isopropanol (2×300 g). The solvent was removed by rotary evaporation. A saturated sodium bicarbonate solution (2.0 L) was then transferred to the flask, and the mixture was extracted with a second portion of ethyl acetate (1.5 L). The organics were combined (transparent, red-orange), and dried overnight over sodium sulfate (270 g). the solution was filtered and the solvent was removed by rotary evaporation to yield the titled compound 4 as a yellow powder (312.3 g, 96%). $^1$H NMR (400 MHz, DMSO), δ 8.85 (m, 2H), 8.35 (m, 5H), 8.25 (m, 1H), 2.95 (t, 2H, J=7 Hz), 1.78 (m, 2H), 0.95 (t, 3H, J=7 Hz). MS [M+H]$^+$=296 m/z.

EXAMPLE 3

Synthesis of N-(4-(2-(2-propylpyridin-4-yl)thiazol-4-yl)phenyl)methanesulfonamide 5

A 2 liter round bottom flask, equipped with a Claisen head, magnetic stirring, and nitrogen inlet, was charged with compound 4 (74.3 g, 252 mmol) and dichloromethane (750 mL). Pyridine (59.7 g, 755 mmol) was added followed by methane sulfonyl chloride (31.7 g, 277 mmol) over a period of 12 min. The reaction was allowed to stir for 1 h at room temperature, and the TLC (acetone/hexanes 1:1) showed no starting material remaining. The reaction mixture was concentrated by rotary evaporation. Water (4.3 L) was added to the residue and the mixture was extracted with ethyl acetate (2.8 L). The organic layers were combined, dried over sodium sulfate (185 g), and reduced by rotary evaporation followed by high vacuum pump to yield the titled compound 5 as a yellow fluffy solid (80.9 g, 86%). $^1$H NMR (400 MHz, DMSO), δ 9.91 (s, 1H), 8.60 (d, 1H, J=6 Hz), 8.20 (s, 1H), 8.00 (d, 2H, J=10 Hz), 7.78 (m, 1H), 7.73 (m, 1H), 7.30 (d, 2H, J=10 Hz), 3.05 (s, 3H), 2.75 (t, 2H, J=8 Hz), 1.72 (m, 2H), 0.90 (t, 3H, J=8 Hz). MS [M+H]$^+$=374 m/z.

EXAMPLE 4

Synthesis of N-isopropyl-4-(2-(2-propylpyridin-4-yl)thiazol-4-yl)benzenamine 6

2 liter round bottom flask, equipped with magnetic stirring and nitrogen inlet, was charged with compound 4 (72.2 g, 244 mmol) and dichloromethane (720 mL). Acetone (57.0 g, 978 mmol) was added, followed by acetic acid (58.7 g, 978 mmol). The reaction mixture was allowed to stir for 1 hour at room temperature. Sodium triacetoxyborohydride (64.7 g, 306 mmol) was added as a solid over 10 min. The reaction mixture was stirred for 2 hours after which TLC (acetone/hexanes 1:1) showed a small amount of starting material remaining. An additional portion of Sodium triacetoxyborohydride (15.0 g, 71 mmol) was added, and the reaction was allowed to stir for 1 h. TLC analysis showed no starting material remaining. The reaction mixture was added slowly to a saturated sodium bicarbonate solution (1.5 L) in a 4 L beaker. The mixture was stirred for 15 min, stirring was stopped, and the layers were allowed to separate. The lower organic phase was collected and dried overnight (sodium sulfate, 150 g), and reduced by rotary evaporation, as the solvent was exchanged with heptanes (1 L). The mixture was concentrated and the product was collected to give the titled compound 6 as a waxy yellow solid (78.5 g, 95%). $^1$H NMR (400 MHz, DMSO), δ 8.58 (d, 1H, J=6 Hz), 7.85 (s, 1H), 7.75 (m, 3H), 7.69 (m, 1H), 6.61 (d, 2H, J=9 Hz), 3.52 (m, 1H), 2.77 (t, 2H, J=8 Hz), 1.72 (m, 2H), 1.12 (d, 6H, J=8 Hz), 0.90 (t, 3H, J=8 Hz). MS [M+H]$^+$=m/z.

The present invention is well adapted to attain the ends and advantages mentioned as well as those that are inherent therein. The particular embodiments disclosed above are illustrative only, as the present invention may be modified and practiced in different but equivalent manners apparent to those skilled in the art having the benefit of the teachings herein. Furthermore, no limitations are intended to the details of construction or design herein shown, other than as described in the claims below. It is therefore evident that the particular illustrative embodiments disclosed above may be altered or modified and all such variations are considered within the scope and spirit of the present invention.

What is claimed is:

1. A method for synthesizing a polycyclic derivative of a thiazole where the polycyclic thiazole derivative is according to Formula (I):

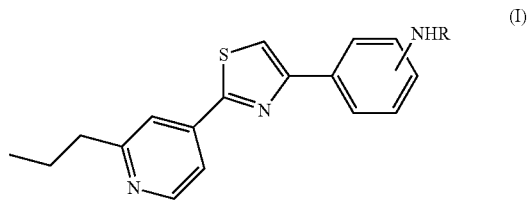

wherein R is H, methyl, isopropyl, benzyl, cyclohexyl, cyclopropylmethyl, acetyl, tert-butyloxycarbonyl, methanesulfonyl, p-toluenesulfonyl, quinolinesulfonyl, or thiophenesulfonyl, comprising the steps of:
(a) reducing the nitro group of a nitrophenyl substituted thiazole according to the chemical structure

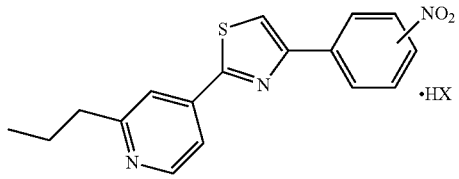

wherein X is a halogen;
to form the polycyclic thiazole derivative according to Formula (I) wherein R is H, and wherein the reducing comprises reacting the nitro group with an iron metal and catalytic ammonium hydroxide; and
(b) when R is methyl, isopropyl, benzyl, cyclohexyl, cyclopropylmethyl, acetyl, tert-butyloxycarbonyl, methanesulfonyl, p-toluenesulfonyl, quinolinesulfonyl, or thiophenesulfonyl, derivatizing the polycyclic thiazole derivative of step (a);
to produce the polycyclic thiazole derivative according to Formula (I).

2. The method of claim 1, further comprising recovering the polycyclic thiazole derivative according to Formula (I).

3. The method of claim 1, further comprising a synthesizing step before step (a) wherein the nitrophenyl substituted thiazole is synthesized by condensing prothionamide with a halo nitroacetophenone to form the nitrophenyl substituted thiazole.

4. The method of claim 3, wherein said synthesizing step comprises heating a mixture of about 1:1 mole ratio of the prothionamide and the halo nitroacetophenone in acetonitrile.

5. The method of claim 4, wherein said halo nitroacetophenone is 2-bromo-4'-nitroacetophenone.

6. The method of claim 1, wherein the polycyclic thiazole derivative according to Formula (I) is

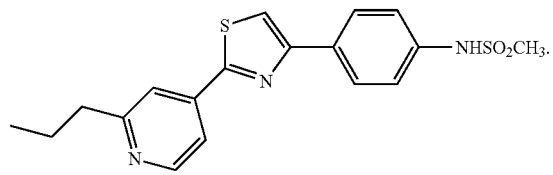

7. The method of claim 1, wherein the polycyclic thiazole derivative according to Formula (I) is

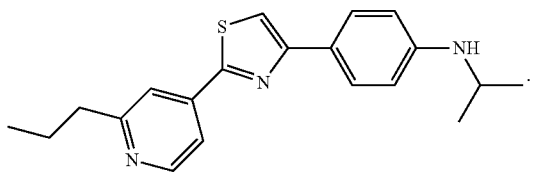 [SMILES: CCCc1cc(-c2nc(-c3ccc(NC(C)C)cc3)cs2)ccn1]

8. The method of claim 3 where the polycyclic thiazole derivative according to Formula (I) is:

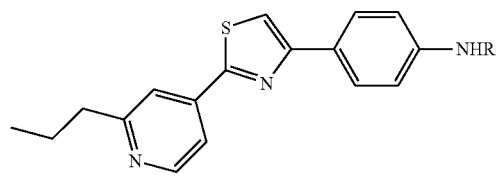

and wherein the nitrophenyl substituted thiazole of step (a) is according to the chemical structure

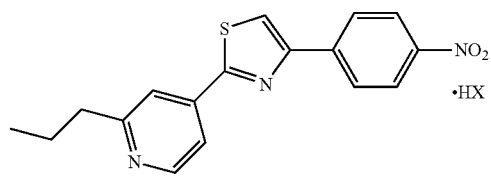

wherein X is a halogen.

9. The method of claim 8, further comprising recovering the polycyclic thiazole derivative according to Formula (I).

10. The method of claim 8, wherein the halo nitroacetophenone is 2-bromo-4'-nitroacetophenone, said synthesizing step before step (a) comprises heating a mixture of the prothionamide and the 2-bromo-4'-nitroacetophenone in acetonitrile in a mole ratio of about 1:1.

11. The method of claim 3, wherein the polycyclic thiazole derivative of step (a), is

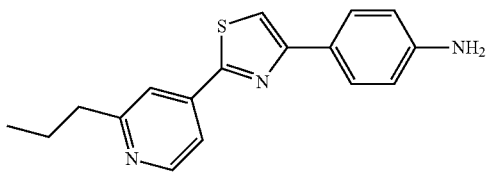 [SMILES: CCCc1cc(-c2nc(-c3ccc(N)cc3)cs2)ccn1]

and is derivatized and said derivatizing step (b) comprises reacting

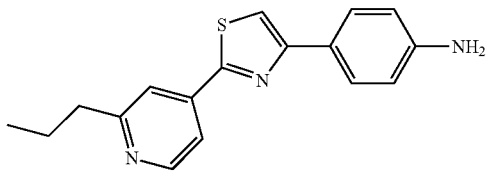 [SMILES: CCCc1cc(-c2nc(-c3ccc(N)cc3)cs2)ccn1]

with methanesulfonyl chloride and a base to produce the polycyclic thiazole derivative according to Formula (I):

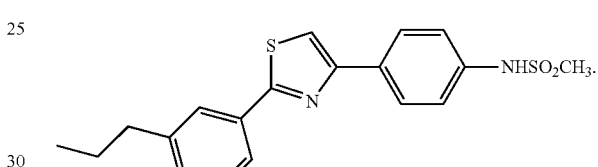

12. The method of claim 11, wherein said base is pyridine.

13. The method of claim 3, wherein said derivatizing step (b) comprises reductively aminating a carbonyl compound with the polycyclic thiazole derivative of step (a),

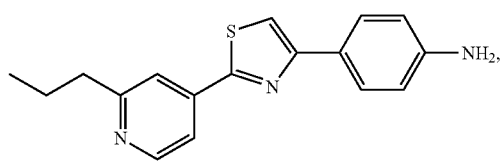 [SMILES: CCCc1cc(-c2nc(-c3ccc(N)cc3)cs2)ccn1]

in the presence of a reducing agent to produce the polycyclic thiazole derivative according to Formula (I) where R is methyl, isopropyl, benzyl, cyclohexyl, or cyclopropylmethyl.

14. The method of claim 13, wherein said carbonyl compound is acetone and said reducing agent is sodium triacetoxyborohydride.

15. The method of claim 13, wherein said polycyclic thiazole derivative is

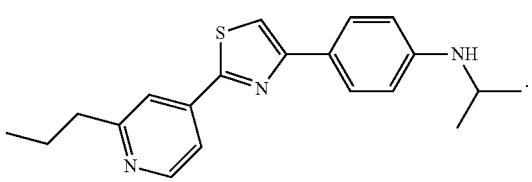 [SMILES: CCCc1cc(-c2nc(-c3ccc(NC(C)C)cc3)cs2)ccn1]

* * * * *